United States Patent
Ryder et al.

(10) Patent No.: US 6,919,317 B2
(45) Date of Patent: Jul. 19, 2005

(54) PHARMACEUTICAL COMPOSITION COMPRISING SQUALENE EPOXIDASE INHIBITOR AND MACROLIDE IMMUNOMODULATOR

(75) Inventors: Neil Stewart Ryder, Vienna (AT); Friedrich Karl Mayer, Oberwil (CH)

(73) Assignee: Novartis AG, Basel (CH)

( * ) Notice: Subject to any disclaimer, the term of this patent is extended or adjusted under 35 U.S.C. 154(b) by 46 days.

(21) Appl. No.: 10/204,027

(22) PCT Filed: Feb. 16, 2001

(86) PCT No.: PCT/EP01/01744

§ 371 (c)(1),
(2), (4) Date: Oct. 9, 2002

(87) PCT Pub. No.: WO01/60345

PCT Pub. Date: Aug. 23, 2001

(65) Prior Publication Data

US 2003/0100517 A1 May 29, 2003

(30) Foreign Application Priority Data

Feb. 18, 2000 (GB) .............................................. 0003932

(51) Int. Cl.⁷ ......................... A01N 43/04; A01N 33/02; A61K 31/70; A61K 31/135
(52) U.S. Cl. ............................. 514/27; 514/28; 514/29; 514/30; 514/31; 514/649; 514/650; 514/655; 536/7.1; 536/7.2; 564/387
(58) Field of Search .............................. 514/27, 28, 29, 514/30, 31, 649, 650, 655, 657; 536/7.1, 7.2; 564/387

(56) References Cited

U.S. PATENT DOCUMENTS 5,985,906 A * 11/1999 Meingassner et al. ...... 514/383
2001/0003589 A1 * 6/2001 Neuer et al. ................ 424/456

FOREIGN PATENT DOCUMENTS

EP 0427680 B1 5/1991
EP 0515310 A1 11/1992

* cited by examiner

*Primary Examiner*—James O. Wilson
*Assistant Examiner*—Traviss C. McIntosh, III
(74) *Attorney, Agent, or Firm*—Gregory C. Houghton

(57) ABSTRACT

Synergistic combinations of a squalene epoxidase inhibitor such as terbinafine and a macrolide T-cell immunomodulator or immunosuppressant such as 33-epichloro, 33-desoxyascomycin are provided, which are useful in particular in the treatment of diseases involving fungal or suspected fungal infection, for immunomodulation or immunosuppression in conditions in which fungal or suspected fungal colonisation of e.g. the skin plays a role, such as atopic dermatitis and seborrhoeic dermatitis, and in situations of fungal resistance.

7 Claims, No Drawings

PHARMACEUTICAL COMPOSITION COMPRISING SQUALENE EPOXIDASE INHIBITOR AND MACROLIDE IMMUNOMODULATOR

The invention relates to pharmaceutical compositions, for use in particular against fungal infections.

It concerns a pharmaceutical composition comprising a squalene epoxidase inhibitor in combination with a macrolide T-cell immunomodulator or immunosuppressant.

While an antifungal activity is known for various macrolide T-cell immunomodulators and immunosuppressants, and some such macrolides have even first been disclosed in the literature as antifungals, e.g. ascomycin and rapamycin, their antifungal activity has been viewed mostly as being largely coincidental with their immunomodulating properties, and further, no common pattern was known, the structural and mechanistic similarities between these compounds having been discovered only long after their original isolation. In particular, notwithstanding the antifungal heritage of macrolide T-cell immunomodulators and immunosuppressants, no significant reports have appeared in the literature on any potentiating effect on the antifungal activity of squalene epoxidase inhibitors, nor are synergistic pharmaceutical compositions comprising these two classes of drugs in combination known.

It has now been found that, surprisingly, when used in combination, squalene epoxidase inhibitors and macrolide T-cell immunomodulators and immunosuppressants act synergistically, resulting in a potentiation of pharmacological activity, so that effective beneficial, especially antifungal activity is seen upon co-administration at dosages which would be well below the effective dosages individually. Further, with antifungals other than squalene epoxidase inhibitors, in particular azole 14α-methyldemethylase inhibitors, no significant positive interaction with such macrolides is seen, or interaction to a much smaller degree, or even antagonism, as with e.g. fluconazole.

The invention thus concerns novel pharmaceutical compositions comprising a squalene epoxidase inhibitor in association or combination with a macrolide T-cell immunomodulator or immunosuppressant, hereinafter briefly named "the compositions of the invention".

A macrolide T-cell immunomodulator or immunosuppressant is to be understood herein as being a T-cell immunomodulator or T-cell immunosuppressant which has a macrocyclic compound structure including a lactone or lactam moiety. While it preferably has at least some T-cell immunomodulating or immunosuppressant activity, it may also exhibit concomitantly or predominantly further pharmaceutical properties, such as anti-inflammatory activity.

The compositions of the invention may be adapted for systemic, e.g. oral or intravenous, or topical use; preferably topical use. They are useful for the known indications of the particular active agents incorporated therein. They are particularly indicated for use in diseases involving fungal or suspected fungal infections, e.g. by yeasts such as *Candida* or *Malassezia* (*Pityrosporum*) spp., or dermatophyte filamentous fungi such as *Microsporum* spp; or for use in conditions in which fungal or suspected fungal colonisation of e.g. the skin plays a role, optionally in connection with an inflammatory component or inflammatory complications, such as atopic dermatitis and seborrhoeic dermatitis, or in situations of fungal resistance.

A suitable squalene epoxidase inhibitor is for example a thiocarbamate antifungal such as tolnaftate or tolciclate, or an aryl- or heteroarylmethylamine antifungal, preferably of the allyl- or benzylamine class of antifungals, e.g. as described in GB 1, 579, 879, EP 896, EP 24587, GB 2, 116, 171, GB 2, 185, 980, EP 164697, EP 221781 and EP 421302. It is in particular naftifine (Exoderil®) or butenafine (Mentax®), preferably terbinafine (Lamisil®), i.e. (E)-N-methyl-N-(1-naphthylmethyl)-6,6-dimethylhept-2-en-4-amin of formula I

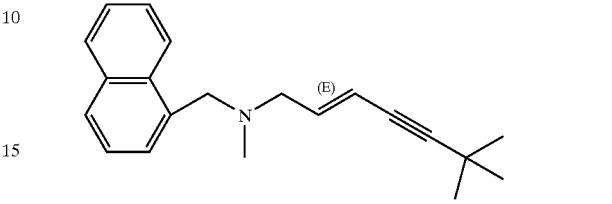

in free form or salt form, particularly hydrochloride acid addition salt form, disclosed as Example 16 in EP 24587.

A suitable macrolide T-cell immunomodulator or immunosuppressant is for example an FKBP12-binding calcineurin inhibitor or mitogen-activated kinase modulator or inhibitor, in particular an asco- or rapamycin. It preferably is an ascomycin. While the macrolide preferably has at least some calcineurin- or mitogen-activated kinase modulating or inhibiting activity, it may also exhibit concomitantly or predominantly further pharmaceutical properties, such as antiinflammatory activity. It preferably is a compound, e.g. an ascomycin, having rather long-acting activity relatively to other members of the same structural class, e.g. it is degraded metabolically slowly to inactive products.

An asco- or rapamycin is to be understood as asco- or rapamycin as such, or a derivative thereof. A derivative is to be understood as being an antagonist, agonist or analogue of the parent compound which retains the basic structure and modulates at least one of the biological, for example immunological properties of the parent compound.

Suitable ascomycins are e.g. as described in EP 184162, EP 315978, EP 323042, EP 423714, EP 427680, EP 465426, EP 474126, WO 91/13889, WO 91/19495, EP 484936, EP 523088, EP 532089, EP 569337, EP 626385, WO 93/5059 and WO 97/8182;

in particular:
  ascomycin;
  tacrolimus (FK506; Prograf®);
  imidazolylmethoxyascomycin (WO 97/8182 in Example 1 and as compound of formula I);
  32-O-(1-hydroxyethylindol-5-yl)ascomycin (L-732531) (*Transplantation* 65 [1998] 10–18, 18–26, on page 11, FIG. 1; and
  (32-desoxy,32-epi-N1-tetrazolyl)ascomycin (ABT-281) (*J. Invest. Dermatol.* 12 [1999] 729–738, on page 730, FIG. 1);

preferably:
  {1R,5Z,9S,12S-[1E-(1R,3R,4R)],13R,14S,17R,18E,21S,23S,24R,25S,27R}-17-ethyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0(4,9)]octacos-5,18-diene-2,3,10,16-tetraone (Example 8 in EP 626385),
    hereinafter referred to as "5,6-dehydroascomycin";
  {1E-(1R,3R,4R)]1R,4S,5R,6S,9R,10E,13S,15S,16R,17S,19S,20S}-9-ethyl-6,16,20-thihydroxy-4-[2-(4-hydroxy-3-methoxycyclohexyl)-1-methylvinyl]-15,17-dimethoxy-5,11,13,19-tetramethyl-3-oxa-22- azatricyclo[18.6.1.0(1,22)]heptacos-10-ene-2,8,21,27-tetraone (Examples 6d and 71 in EP 569337), hereinafter referred to as "ASD 732"; and pimecrolimus (INN recommended) (ASM981; Elidel™), i.e {[1E-(1R,3R,4S)]1R,9S,12S, 13R,14S,17R,18E, 21S,23S,24R,25S,27R}-12-[2-(4-chloro-3-methoxycyclohexyl)-1-methylvinyl]-17-ethyl-1,14-dihydroxy-23,25-dimethoxy-13,19,21,27-tetramethyl-11,28,dioxa-4-azatricyclo [22.3.1.0(4,9)]octacos-18-ene-2,3,10,16-tetraone, of formula I

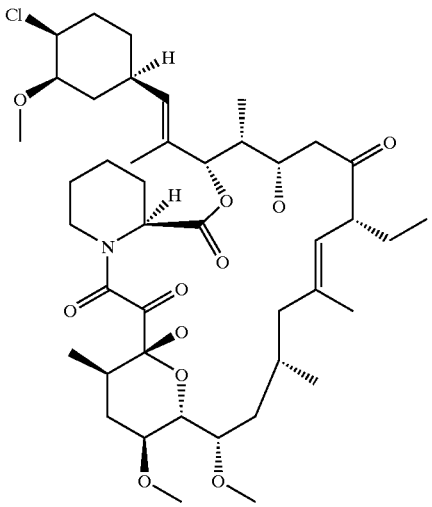

(Example 66a in EP 427680),
hereinafter referred to as "33-epichloro,33-desoxyascomycin".

Suitable rapamycins are e.g. as described in U.S. Pat. No. 3,929,992, WO 94/9010 and U.S. Pat. No. 5,258,389, preferably sirolimus (rapamycin; Rapamune®) and everolimus (RAD001; Certican®).

Particularly preferred are compositions of the invention comprising an arylmethylamine antifungal in combination with an ascomycin, especially terbinafine in combination with 33-epichloro,33-desoxyascomycin.

Preferred for use in the treatment of conditions where inflammation is involved are compositions of the invention wherein one or both components possess some degree of inherent anti-inflammatory activity, such as naftifine or terbinafine in combination with 33-epichloro,33-desoxyascomycin.

"Treatment" as used herein includes prevention, namely prophylactic as well as curative treatment.

Synergy is e.g. calculated as described in Example 1 hereunder or as described in Berenbaum, Clin. Exp. Immunol. 28 (1977) 1, using an interaction term to correct for differences in mechanism between the two drugs, as described in Chou et al., Transpl. Proc. 26 (1994) 3043. The index of synergy is calculated as:

$$\frac{\text{dose of } A}{A_E} + \frac{\text{dose of } B}{B_E} + \frac{(\text{dose of } A) \times (\text{dose of } B)}{A_E \times B_E}$$

in which the doses of the compounds A and B represent those used in a particular combination, and $A_E$ and $B_E$ are the individual doses of A and B respectively giving the same effect. If the result is less than 1, there is synergy; if the result is 1, the effect is additive; if the result is greater than 1, A and B are antagonistic. By plotting an isobologram of dose of $A/A_E$ vs. dose of $B/B_E$, the combination of maximum synergy can be determined. The synergistic ratio expressed in terms of the ratio by weight of the two compositions at synergistic amounts along the isobologram, especially at or near the point of maximum synergy, can then be used to determine formulations containing an optimally synergistic ratio of the two compounds.

The invention also provides products and methods for co-administration of a squalene epoxidase inhibitor, e.g. terbinafine and a macrolide T-cell immunomodulator or immunosuppressant, e.g. 33-epichloro,33-desoxyascomycin or 5,6-dehydroascomycin, at synergistically effective dosages, e.g.:

a method of treatment or prevention of diseases involving a fungal or suspected fungal infection, or a method for immunomodulation or immunosuppression in a condition in which fungal or suspected fungal colonization plays a role or in situations of fungal resistance; in a subject suffering from or at risk for such infection or condition, comprising co-administering synergistically effective amounts of a composition of the invention;

the use of a squalene epoxidase inhibitor in the manufacture of a medicament for co-administration in synergistically effective amounts with a macrolide T-cell immunomodulator or immunosuppressant;

the use of a macrolide T-cell immunomodulator or immunosuppressant in the manufacture of a medicament for co-administration in synergistically effective amounts with a squalene epoxidase inhibitor;

a kit of parts comprising a squalene epoxidase inhibitor and a macrolide T-cell immunomodulator or immunosuppressant in separate unit dosage forms, preferably wherein the unit dosage forms are suitable for administration of the component compounds in synergistically effective amounts, together with instruction for use, optionally with further means for facilitating compliance with the administration of the component compounds, e.g. a label or drawings;

the use of a squalene epoxidase inhibitor in the manufacture of a pharmaceutical kit which is to be used for facilitating co-administration with a macrolide T-cell immunomodulator or immunosuppressant;

the use of a macrolide T-cell immunomodulator or immunosuppressant in the manufacture of a pharmaceutical kit which is to be used for facilitating co-administration with a squalene epoxidase inhibitor;

a squalene epoxidase inhibitor and a macrolide T-cell immunomodulator or immunosuppressant as a combined pharmaceutical preparation for simultaneous, separate or sequential use, preferably in synergistically effective amounts, e.g. for the treatment or prevention of a fungal infection, or for immunomodulation or immunosuppression in a condition in which fungal or suspected fungal colonization plays a role;

a pharmaceutical composition comprising a squalene epoxidase inhibitor in combination or association with a macrolide T-cell immunomodulator or immunosuppressant, e.g. in synergistically effective amounts, together with at least one a pharmaceutically acceptable diluent or carrier, e.g. for use in treatment or prevention of a fungal infection, or for immunomodulation or immunosuppression in a condition in which fungal or suspected fungal colonization plays a role, or in a situation of fungal resistance; and a process for the preparation of a composition of the invention comprising mixing a squalene epoxidase inhibitor and a macrolide T-cell immunomodulator or immunosuppressant, in combination or association with at least one pharmaceutically acceptable diluent or carrier.

By "synergistically effective amounts" is meant an amount of squalene epoxidase inhibitor and an amount of macrolide T-cell immunomodulator or immunosuppressant which are individually below their respective effective dosages for a relevant indication, but which are pharmaceutically active on co-administration, e.g. in a synergistic ratio, for example as calculated above. Furthermore, "synergistically effective amounts" may mean an amount of squalene epoxidase inhibitor and an amount of macrolide T-cell immunomodulator or immunosuppressant which are individually equal to their respective effective dosages for a relevant indication, and which result in a more than additive effect.

The molar amount of squalene epoxidase inhibitor present is from roughly similar to, to significantly more than the amount of macrolide T-cell immunomodulator or immunosuppressant, preferably twice as much or more. Synergistic ratios of squalene epoxidase inhibitor to macrolide T-cell immunomodulator or immunosuppressant by weight are thus suitably from about 1:10 to about 50:1, preferably from about 1:5 to about 20:1, most preferably from about 1:1 to about 15:1, e.g. about 12:1.

The compositions of the invention can be administered as a free combination, or the drugs can be formulated into a fixed combination, which greatly enhances the convenience for the patient.

Absolute dosages of the compounds will vary depending on a number of factors, e.g. the individual, the route of administration, the desired duration, the rate of release of the active agent and the nature and severity of the condition to be treated. For example, the amount of active agents required and the release rate thereof may be determined on the basis of known in vitro and in vivo techniques, determining how long a particular active agent concentration in the blood plasma remains at an acceptable level for a therapeutic effect.

For example, in prevention and treatment of fungal or suspected fungal infection, an initial dosage of about 2–3 times the maintenance dosage is suitably administered, followed by a daily dosage of about 2–3 times the maintenance dosage for a period of from one to two weeks, and subsequently the dose is gradually tapered down at a rate of about 5% per week to reach the maintenance dosage. In general, synergistically effective amounts of terbinafine and 33-epichloro,33-desoxyascomycin on oral administration for use in prevention and treatment of fungal diseases in larger animals, e.g. man, are amounts of terbinafine of up to about 50 mg/kg/day, e.g. from about 0.25 mg/kg/day to about 50 mg/kg/day, preferably about 2.5 mg/kg/day, in combination or co-administration with amounts of 33-epichloro,33-desoxyascomycin of up to about 2 mg/kg/day, e.g. from about 0.01 mg/kg/day to about 2 mg/kg/day, preferably about 0.5 mg/kg/day, in a synergistic ratio, as described. Suitable unit dosage forms for oral co-administration of these compounds thus may contain on the order of from about 10 mg to about 3000 mg, preferably about 50 mg to about 500 mg of terbinafine, and from about 0.5 mg to about 100 mg, preferably about 3 mg to about 30 mg of 33-epichloro,33-desoxyascomycin. The daily dosage for oral administration is preferably taken in a single dose, but may be spread out over two, three or four dosages per day. For i.v. administration, the effective dosage is lower than that required for oral administration, e.g. about one fifth the oral dosage.

By "co-administration" is meant administration of the components of the compositions of the invention together or at substantially the same time, e.g. within fifteen minutes or less, either in the same vehicle or in separate vehicles, so that upon oral administration, for example, both compounds are present simultaneously in the gastrointestinal tract. Preferably, the compounds are administered as a fixed combination.

The compositions of the invention include compositions suitable for administration by any conventional route, in particular compositions suitable for administration either enterally,. for example, orally, e.g. in the form of solutions for drinking, tablets or capsules, or parenterally, e.g. in the form of injectable solutions or suspensions; or topically, e.g. for the treatment of fungal conditions of the skin or mucosae, e.g. in the form of a dermal cream, ointment, ear drops, mousse, shampoo, solution, lotion, gel, emulgel or like preparation, e.g. in a concentration of from about 0.1% to about 2% by weight of each component, especially in combination or association with penetration enhancing agents, as well as for application to the eye, e.g. in the form of an ocular cream, gel or eye-drop preparation, for treatment of fungal or suspected fungal conditions of the lungs and airways, e.g. in the form of inhalable compositions, and for mucosal application, e.g. in the form of vaginal tablets.

The compositions of the invention are suitably emulsions, microemulsions, emulsion preconcentrates or microemulsion preconcentrates, or solid dispersions, especially water-in-oil microemulsion preconcentrates or oil-in-water microemulsions, comprising the squalene epoxidase inhibitor and the macrolide T-cell immunomodulator or immunosuppressant in a synergistic ratio.

The compositions of the invention can be prepared in conventional manner, e.g. by mixing a squalene epoxidase inhibitor and a macrolide T-cell immunomodulator or immunosuppressant, in combination or association with at least one pharmaceutically acceptable diluent or carrier.

The active agent components may be in free form or pharmaceutically acceptable salt form as appropriate.

The following Examples illustrate the invention. All temperatures are in degrees Celsius. The compounds are in free, i.e. neutral or base form unless specified otherwise. The following abbreviations are used:

| | |
|---|---|
| BSA = | bovine serum albumin |
| cfu = | colony-forming units |
| FKBP12 = | FK-binding protein 12 |
| MIC = | minimum inhibitory concentration |
| MOPS = | 3-(N-morpholino)propanesulfonic acid |

EXAMPLE 1

Synergism in Yeast (*Candida*)

Combination studies are performed with Candida species, using the NCCLS standard assay (National Committee for Clinical Laboratory Standards [1995], *Reference method for broth dilution antifungal susceptibility testing of yeasts* (Tentative Standard M27-T, NCCL, Villanova, Pa., U.S.A.), modified as follows: the assay is effected in RPMI 1640 medium without NaHCO$_3$ but with L-glutamine buffered with MOPS at pH 7.0 at 37°. The inoculum is $2.5 \times 10^3$ cfu/ml. Incubation times are 48 hours. The MIC is defined as the lowest drug concentration causing 80% inhibition of fungal growth.

The reference test compound (either terbinafine or fluconazole) is tested in a full concentration range in the absence or presence of the other test drug at 1, 2, 4, and 8 µg/ml.

Interaction between the drugs is analysed by calculation of the Fractional Inhibitory Concentration Index (FICI), defined as:

FICI=[(MIC A in combination)/MIC A]+[MIC B in combination]/MIC B]

Interpretation of FICI in terms of interaction between the two drugs is as follows: FICI=0.5: synergy; <0.5<FICI=1: additive; 1<FICI=2: indifferent; 2<FICI: antagonism (in practical terms, synergy by this definition means that the MICs of both drugs are reduced by at least 2 dilution steps when used in combination).

The ability of the four test compounds 33-epichloro,33-desoxyascomycin, 5,6-dehydroascomycin, ascomycin and tacrolimus to influence the antifungal activity of terbinafine and fluconazole was examined in a *Candida albicans* isolate susceptible to both drugs, and in one isolate of *Candida krusei* which is resistant to terbinafine and poorly responsive to fluconazole. The test compounds alone are completely inactive against both strains. The Table summarises the patterns of interactions which have been obtained:

TABLE 1

Interaction of macrolide 33-epichloro,33-desoxyascomycin with terbinafine or with fluconazole in Candida yeast

| Compound | Interaction with terbinafine[a] | | Interaction with fluconazole[a] | |
|---|---|---|---|---|
|  | C. albicans | C. krusei | C. albicans | C. krusei |
| 33-Epichloro,33-desoxy-ascomycin | + | − | − | − |
| 5,6-Dehydro-ascomycin | + | − | − | − |
| Ascomycin | + | (* | − | − |
| Tacrolimus | + | (* | − | − |

[a]The symbols refer to the interpretation of the FICI value, as described in this Example, and mean: (*: synergy; +: additive; −: indifferent/antagonistic)

With terbinafine as reference compound, all four test compounds show potent interaction against *Candida albicans*, while ascomycin and tacrolimus are powerfully synergistic with terbinafine against *Candida krusei*, and 33-epichloro,33-desoxy-ascomycin and 5,6-dehydroascomycin are also strongly positive. A different pattern is seen with fluconazole, which shows no potent synergy, and is antagonistic in many cases.

EXAMPLE 1a

Synergism in Dermatophyte (*Microsporum canis*)

Minimum Inhibitory Concentrations (MIC) against dermatophytes are determined in 96-well assay trays by a modification of the NCCLS microdilution procedure M38-P (National Committee for Clinical Laboratory Standards, Reference method for broth antifungal susceptibility testing of conidium-forming filamentous fungi; NCCLS document M38-P; NCCLS, Wayne, Pa., USA [1998]), as detailed in H. A. Norris et al., *J. Am. Acad. Dermatol.* 40 [1999] S9–S13). The MIC is defined as the lowest drug concentration causing 80% inhibition of fungal growth.

Combination studies are performed in a checkerboard design using the above assay to provide a matrix of all possible dose combination of the two drugs within the required concentration range. The matrix structure is provided by the microtiter trays used for the assay. The terbinafine dilution series is arranged on the y-axis (in columns) and the partner drug on the x-axis (in rows). In each row, well no. 1 contains the sterility control, well no. 2 contains terbinafine hydrochloride alone, wells no. 3 to no. 11 contain the dilution series of the partner drug 33-epichloro,33-desoxyascomycin, and well no. 12 contains the growth control. In each column, well A contains the partner drug alone and wells B to H contain the dilution series of terbinafine hydrochloride.

The nature of the interaction between the two drugs is defined quantitatively by means of the Fractional Inhibitory Concentration Index (FICI), which is calculated by the following formula:

FICI=[(MIC A in combination)/MIC A]+[(MIC B in combination)/MIC B].

Interpretation of the FICI is:

≦0.5: synergy;
>0.5 but ≦1: additive;
>1 but ≦2: indifferent;
>2: antagonism.

In practice, synergy calculated in this way is equivalent to a reduction of at least 2 dilution steps in the MIC of each drug when they are combined.

The results obtained with *Microsporum canis* (strain NFI 5167) are indicated in Table 2:

TABLE 2

Interaction of macrolide 33-epichloro,33-desoxyascomycin with terbinafine hydrochloride in dermatophyte *Microsporum canis*

| MIC single drug | | MIC combination | | | |
|---|---|---|---|---|---|
| terbinafine | partner | terbinafine | partner | FICI | Interpretation |
| 0.031 | 64 | 0.001 | 16.000 | 0.28 | synergy |

EXAMPLE 2

Tablet

A tablet for oral use with granulated terbinafine hydrochloride and 33-epichloro,33-desoxyascomycin in form of a solid dispersion is prepared in conventional manner, in a 600 mg dosage, and contains the following ingredients:

| Component | Amount (mg) |
|---|---|
| 33-Epichloro,33-desoxyascomycin | 20.0 |
| Terbinafine hydrochloride | 281.25 |
| | (corresponds to 250 mg free base) |
| Silicium dioxide colloidal (Aerosil 200) | 1.95 |
| Microcrystalline cellulose | 48.30 |
| Sodium carboxymethyl starch | 35.10 |
| Hydroxypropylmethyl cellulose 3 cps | 81.70 |
| Poloxamer 188 | 10.00 |
| Lactose, anhydrous | 67.50 |
| Crospovidone | 50.00 |
| Magnesium stearate | 4.20 |
| Total | 600.00 |

EXAMPLE 3

Cream

A cream with dissolved terbinafine base is prepared in conventional manner with 33-epichloro,33-desoxyascomycin, both in a 1% w/w concentration, and contains the following ingredients:

| Component | Amount (g) |
|---|---|
| 33-Epichloro,33-desoxyascomycin | 1.00 |
| Terbinafine base | 1.00 |
| Triglycerides, medium chain | 15.00 |
| Oleyl alcohol | 10.00 |
| Sodium cetylstearyl sulfate | 1.00 |
| Cetyl alcohol | 4.00 |
| Stearyl alcohol | 4.00 |
| Glyceryl monostearate | 2.00 |
| Benzyl alcohol | 1.00 |
| Propylene glycol | 5.00 |
| Citric acid | 0.05 |
| Sodium hydroxide | 0.02 |
| Water | 55.93 |
| Total | 100.00 |

EXAMPLE 4

Ointment

An ointment with terbinafine hydrochloride and 33-epichloro,33-desoxyascomycin in suspended form is prepared in conventional manner in a 1% w/w concentration, and contains the following ingredients:

| Component | Amount (g) |
|---|---|
| 33-Epichloro,33-desoxyascomycin | 1.00 |
| Terbinafine hydrochloride | 1.125 |
| Mineral oil | 45.00 |
| Petrolatum | 42.875 |
| Microcrystalline wax | 10.00 |
| Total | 100.00 |

EXAMPLE 5

Vaginal Tablet

A tablet for vaginal use with granulated terbinafine hydrochloride and 33-epichloro,33-desoxyascomycin is prepared in conventional manner, in a 1600 mg dosage, and contains the following ingredients:

| Component | Amount (mg) |
|---|---|
| 33-Epichloro,33-desoxyascomycin | 20.0 |
| Terbinafine hydrochloride | 281.25 (corresponds to 250 mg free base) |
| Lactose monohydrate | 1004.75 |
| Sodium carboxymethyl starch | 96.00 |
| Hydroxypropylmethyl cellulose 3 cps | 54.00 |
| Corn starch | 112.0 |
| Magnesium stearate | 32.00 |
| Total | 1600.00 |

Terbinafine in Examples 2 to 5 may be replaced by a molar equivalent amount of tolnaftate, tolciclate, naftifine or butenafine.

33-Epichloro,33-desoxyascomycin in Examples 2 to 5 may be replaced by a molar equivalent amount of ascomycin, tacrolimus, imidazolylmethoxyascomycin, 32-O-(1-hydroxyethylindol-5-yl)ascomycin, (32-desoxy,32-epi-N1-tetrazolyl)ascomycin, 5,6-dehydroascomycin, ASD 732, sirolimus or everolimus.

What is claimed is:

1. A pharmaceutical composition comprising a combination of a squalene epoxidase inhibitor selected from a thiocarbamate antifungal or an arylmethylamine or heteroarylmethylamine antifungal and a macrolide T-cell immunomodulator or immunosuppressant which has a macrocyclic compound structure including a lactone or lactame moiety and is an ascomycin or rapamycin, as active ingredients, together with at least one pharmaceutically acceptable diluent or carrier, wherein said squalene epoxidase inhibitor and said macrolide T-cell immunomodulator or immunosuppressant of said composition can be administered at substantially the same time or in combination.

2. A composition according to claim 1 comprising terbinafine and 33-epichloro, 33-desoxyascomycin.

3. A method of treatment of a disease involving fungal infection, or a method for immunomodulation or immunosuppression in a condition in which fungal colonization plays a role or in a situation of fungal resistance, in a subject suffering from or at risk for such infection or condition, comprising administering a synergistically effective amount of a composition according to claim 1 to a subject in need of such treatment.

4. A process for the preparation of a composition according to claim 1 comprising mixing the squalene epoxidase inhibitor and the macrolide T-cell immunomodulator or immunosuppressant with at least one pharmaceutically acceptable diluent or carrier.

5. A kit of parts comprising a squalene epoxidase inhibitor selected from thiocarbamate antifungal or an aryl- or heteroarylmethylamine antifungal and a macrolide T-cell immunomodulator or immunosuppressant which has a macro cyclic compound structure including a lactone or lactame moiety and is an asco- or rapamycin, in separate unit dosage forms.

6. A composition according to claim 1 wherein said squalene epoxidase inhibitor is terbinafine.

7. A composition according to claim 1 wherein said macrolide T-cell immunomodulator or immunosuppressant is 33-epichloro, 33-desoxyascomycin.

* * * * *